United States Patent [19]
Nakshbendi

[11] 3,972,678

[45] Aug. 3, 1976

[54] APPARATUS FOR CONTROLLING ODORS

[76] Inventor: Ghassan F. Nakshbendi, 300 Central Park Ave., Hartsdale, N.Y. 10530

[22] Filed: Aug. 30, 1974

[21] Appl. No.: 502,090

[52] U.S. Cl. .................................. 21/74 R; 21/53; 21/55; 21/126; 55/307; 55/308
[51] Int. Cl.² ...................... A61L 9/00; A61L 9/01; B01D 39/00
[58] Field of Search ................ 21/74 R, 53, 55, 126; 55/307–309

[56] References Cited
UNITED STATES PATENTS

| | | | |
|---|---|---|---|
| 2,874,032 | 2/1959 | Kuehner | 21/55 X |
| 3,299,620 | 1/1967 | Hollingworth | 21/55 X |
| 3,554,859 | 1/1971 | Murray | 21/55 X |

Primary Examiner—Morris O. Wolk
Assistant Examiner—Dale Lovercheck
Attorney, Agent, or Firm—Friedman & Goodman

[57] ABSTRACT

A method of treating air containing odoriferous substances of both large and small molecular weights includes the step of establishing a flow of the air containing the odoriferous substances. The stream of flowing air is exposed to a bath in the form of a fine spray or mist of a concentrated solution of potassium permanganate at a first treatment zone to primarily oxidize the odoriferous substances having the smaller molecular weights and wash the air. The air is then passed through an adsorbing medium in the form of a bed of activated carbon at a second treatment zone to substantially adsorb and remove the remaining odoriferous substances having the larger molecular weights. Advantageously, the mist or droplets of the spray solution are removed from the air subsequent to movement from the first treatment zone and prior to movement into the second treatment zone. With the method, the air is substantially free of odoriferous substances upon removal from the second treatment zone. The potassium permanganate solution is advantageously recycled and purified so that the same may be efficiently utilized more than once to provide the bath for the stream of air. The apparatus for carrying out the method is described.

4 Claims, 2 Drawing Figures

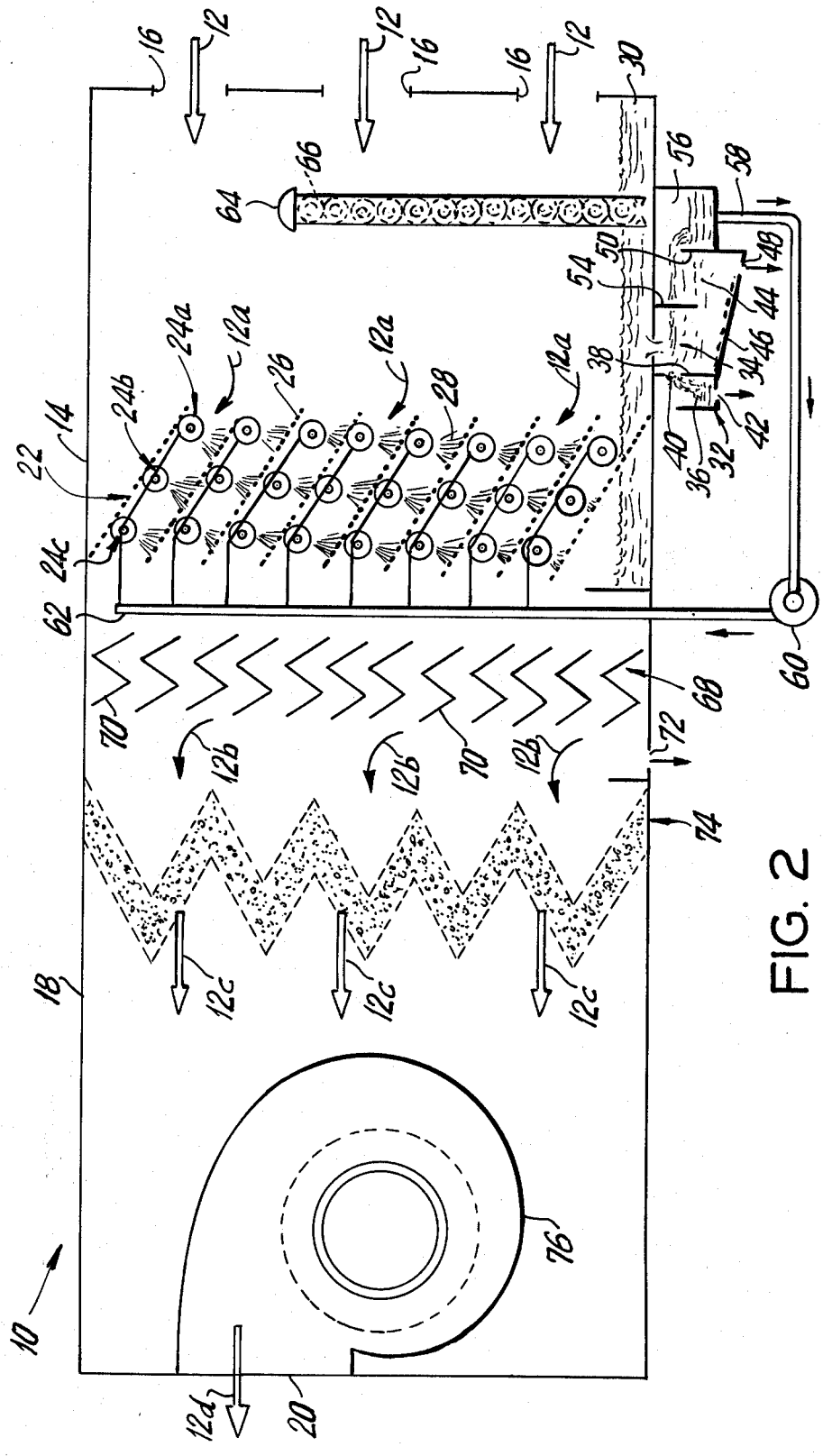

APPARATUS FOR CONTROLLING ODORS

BACKGROUND OF THE INVENTION

This invention generally relates to a method and apparatus for purification of air, and more specifically to a method and apparatus for removing odoriferous substances from air by first exposing the stream of air to a bath of a concentrated solution of potassium permanganate and subsequently passing the air through an adsorbent medium.

Odors generated in homes, offices, light industries, public theatres, etc. are not only composed of organic compounds, but include products of combustion, cooking odors, cigar smoke, dust and other city pollutants.

Odor may be controlled by the following methods: ventilation, combustion, masking and counteraction, destruction by chemical reactions, and removal by sorption and chemisorption.

Open windows have long been the symbol of wholesome indoor living quarters. The method involved — ventilation — is one of the simplest methods of air purification and consists basically in bringing odorous gasses or vapors below a threshhold limit or in certain cases below odor limits at which the human nose can sense. However, ventilation becomes uneconomical in January and other mid-winter months when heating must be provided.

Combustion is most expensive of the methods, and consists of oxidizing or burning at high temperatures the hydrocarbons or organic compounds that most odorous vapors consist of, converting them to $CO_2$ and water vapor. In certain cases, the burning of sulfur and nitrogen containing compounds merely convert them to new oxides that have a higher tolerability limit than the parent compound, and thus are less objectionable. However, due to the fact that combustion normally takes place at 1200 to 1400°F in incinerators and afterburners, and at 500–800°F with the aid of catalysts, combustion becomes practical only in certain instances. For example, combustion may be practical when effluent gasses are well above the ambient temperatures. Also, when waste heat can be economically used for process heating or returned to fuel system for economy; and when the odorants have no economical value and can contribute to heat or combustion.

A further disadvantage of combustion is that it must generally be complete. Incomplete combustion or partial oxidation of some organic compounds produces intermediate oxidation products such as Aldehydes and organic acids that are worse odor offenders.

Masking consists of adding more pleasant odorants to overcome the concentration of existing bad odors. It also can mean adding an anasthetic substances to depress the senses of smell. In this manner, the bad odor is less objectionable. Masking can also be done by blending several odors to diminish the intensity of the original one. Generally, masking involves the blending of two or more odors so that the total odor is increased but is more acceptable.

Counteraction is a method which consists of introducing two antagonistic odors so that when sniffed together, both odors can be diminished or even totally eliminated. Benzene, Toluene, Zylene, and Durene fall into this catagory. In counteraction, the total odor is decreased in intensity, where in masking it is increased in intensity. The disadvantage of both of these methods is that they are highly specialized fields, especially counteraction, and are not easily controlled.

Air borne odorants can be destroyed by a great number of gas, gas-solid or gas-liquid chemical reactions. Two types of chemical groups exist, namely those that are specified reagents for specific contaminants, such as ammonia and acetic acid, and those with broad spectrum reagents for a broad range of contaminants, such as ozone and chlorine. In the use of such chemical reagents, great care must be taken since these reagents may be toxic, corrosive, irritating or odorous, or can produce end products with such properties.

Removal of odoriferous substances may also be achieved by adsorption, wherein adhesion of molecules of gasses takes place to the surface of solid bodies. Adsorption depends on surface area and can become uneconomical when large quantities of air are to be treated. The same observation applies to chemabsorption. When a sorbate enters into chemical reaction with a sorbent, the bond is very strong and difficult and sometimes impossible to reverse. Then two or more sorbates enter into chemical reaction by virtue of their proximity and condensed conditions in the sorbent state, this type of chemabsorption is also called "surface catalysis". The initial capital investment as well as maintainence costs in the use of these two methods is high.

Based on the above review of the existing methods of air purification, it becomes readily clear that no one method can do a complete job of eliminating odors from the air in an economical fashion.

With respect to destruction of odoriferous substances by chemical reactions, it is noted that gas-liquid systems have been mostly available in large commercial plants where air washers with special reagents are used in specific industries and are rare outside of those industries.

Activated carbon is a well known adsorbent and can eliminate odors but works poorly on low concentrations. Another disadvantage of activated carbon is that used alone it cannot remove all odors from the air, particularly the components thereof having smaller molecular weights. The principle of the gas mask has been employed in many instances to eliminate odors and noxious vapors from living and working spaces. Such use have gained momentum in recent years with the introduction of air conditioning. The traditional method of removing odors and correcting a stale and vitiated atmosphere in living quarters is by ventilation with fresh air from outside. As suggested above, the admission of large quantities of outside air, however, can increase the cost of air conditioning to a prohibitive level.

In many situations, therefore, it has become a more general practice to recirculate much of the air and maintain the purity and freshness by passing the air continuously through a bed of granular activated carbon. As suggested above, however, this approach is not suitable, from a practical and economical point of view, where very intense or low concentrations of odoriferous substances are to be removed from air.

The present invention is for a method and apparatus for treating contaminated air efficiently and economically with an effectiveness not achievable with any of the above enumerated methods of purification. Both the initial capital expense, as well as the operation of the device of the present invention is substantially less than that of comparable devices known in the art. A further advantage of the present invention is that the treated air is substantially free of the odoriferous substances as well as free from any additional odors or chemicals which are generated during the treatment process.

The invention which is disclosed in this application deals with a unique method and apparatus of air treatment combining oxidizing, washing and adsorbing the pollutants of such air and rendering it better than 93% pure of foreign matter.

SUMMARY OF THE INVENTION

It is an object of the present invention to provide a method of treating air containing odoriferous substances which does not have the above described disadvantages associated with comparable prior art methods.

It is another object of the present invention to provide a method of the type under discussion which is simple and economical to use.

It is still another object of the present invention to provide a method of treating air which requires a small initial capital expense.

It is yet another object of the present invention to provide a method of the type suggested in the other objects which utilizes a concentrated solution of potassium permanganate in the form of a spray bath to primarily oxidize the odoriferous substances having small molecular weights in one treatment zone, and adsorbing the remaining odoriferous substances having large molecular weights in a second zone to render the air substantially free of odoriferous substances upon removal from the second treatment zone.

It is a further object of the present invention to provide a method as described in the last object which recycles the potassium permanganate solution while purifying and maintaining the same at a constant concentration to provide efficient oxidation of the odoriferous substances having small molecular weights.

It is still a further object of the present invention to provide an apparatus which can carry out the method suggested in the above objects.

To achieve the above objects, as well as others which will become apparent hereafter, a method of treating air containing odoriferous substances in accordance with the present invention comprises the steps of establishing the flow of the air containing the odoriferous substances. The stream of flowing air is exposed to a bath of a concentrated solution of potassium permanganate at a first treatment zone to primarily oxidize the odoriferous substances having the smaller molecular weights. The air is then passed through an adsorbing medium at a second treatment zone to adsorb and remove the remaining odoriferous substances having the larger molecular weights. In this manner, the air treated is substantially free of odoriferous substances upon removal from said second treatment zone.

In the presently preferred embodiment, the stream of air is exposed to the bath in the form of a spray with a fine mist of the potassium permanganate solution. Advantageously, the stream of air is deflected from its normal direction of flow during the spraying step to maintain the air to be treated under the influence of the potassium permanganate mist for a prolonged period of time for any given rate of air flow. Improved results are achieved when the mist is removed from the air subsequent to movement of the air from said first treatment zone and prior to movement to said second treatment zone.

According to a further important feature of the present invention, the solution of potassium permanganate is recycled and utilized more than once to provide the bath for the stream of air. During the recycling step, the potassium permanganate is advantageously purified and the concentration of the potassium permanganate may be strengthened to maintain the concentration at a substantially constant level.

The apparatus of the present invention includes means for establishing the flow of the air containing the odoriferous substances. Means are provided for exposing the stream of air to a bath of concentrated solution of potassium permanganate at a first treatment zone to primarily oxidize the odoriferous substances having the smaller molecular weight. An adsorbing medium is provided at a second treatment zone to adsorb and remove the remaining odoriferous substances having the larger molecular weights when the air is passed therethrough. In the presently preferred embodiment, the means for exposing the stream of air to a bath are in the form of a plurality of spray nozzles which dispenses a spray in the form of a mist through which the air is directed. The adsorbing medium in the presently preferred embodiment is in the form of a bed of activated carbon.

Accordingly, the present invention results in a double step treatment which is simple and economical. A relatively inexpensive oxidizing agent, potassium permanganate, is utilized to effectively treat odoriferous substances having small molecular weights. The bed of activated carbon is effective to remove those odoriferous substances having large molecular weights so that the air is substantially free of odoriferous substances upon removal from the second treatment zone or beyond the bed of activated carbon.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is an idealized block diagram of the present invention, illustrating the admission of air to be treated, followed by a potassium permanganate bath and an adsorption zone wherein the output of the system is pure air; and FIG. 2 is a schematic representation of a presently preferred practical embodiment of the present invention as depicted in FIG. 1.

DESCRIPTION OF THE PREFERRED EMBODIMENTS

Referring to FIG. 1, the present invention is illustrated in an idealized block diagram form. The present invention utilizes the desirable oxidizing characteristics of concentrated potassium permanganate, this being a relatively inexpensive substance and compares favorably with the price of other oxidizing agents utilized for comparable purposes.

In FIG. 1, a flow of air containing odoriferous substances is generally designated by the reference character A. The air and odoriferous substances to be treated are first admitted into a first zone, designated by the reference character B, the first zone being in the nature of a potassium permanganate bath for primarily oxidizing those odoriferous substances having the smaller molecular weights. The stream of air at C now ideally only contains odoriferous substances having odoriferous substances of large molecular weights. This air is next admitted into an adsorption zone D which adsorbs and removes the odoriferous substances having the larger molecular weights. The treated air, at E, is, in the ideal case, free of odoriferous substances upon removal from the second treatment zone D.

As will become evident from the description of FIG. 2, the present method and apparatus combine oxidizing, washing and adsorbing pollutants of such air and rendering it substantially free of foreign odorous matter. It has been observed that potassium permanganate, even in concentrated form, oxidizes larger molecules less effectively than smaller molecules and that it is ineffective even as to particular molecules having small molecular weight. Adsorption is used in a further step to substantially eliminate the remaining molecules which are not oxidized by the bath. Thus, the molecules which resist oxidation by potassium permanganate are extracted from the air by adsorption.

Referring now specifically to FIG. 2, a practical embodiment of the idealized system shown in FIG. 1 will now be described. The treatment apparatus is generally designated by the reference numeral 10.

The apparatus 10 is utilized for treating air 12 which includes odoriferous substances of the type generally enumerated above having both components of large and small molecular weights.

The apparatus 10 includes a chamber 14, which represents the potassium permanganate bath chamber having air inlets 16, followed by an adsorption chamber 18 which is provided with an exit port 20 where the treated air 12d is released. The air flow 12 corresponds to the stream A in FIG. 1 and the potassium permanganate bath B of FIG. 1 corresponds to the bath chamber 14. The air from which there has been removed most particles or elements having small molecular weights is designated by the reference character C in FIG. 1 and by the reference numerals 12b in FIG. 2. The adsorption zone D in FIG. 1 corresponds to the chamber 18 in FIG. 2 and the exit port 20 in FIG. 2 corresponds to the flow of air at E in FIG. 1.

Provided within the chamber 14 is a potassium permanganate solution "air scrubber" 22. The "air scrubber" or wetting arrangement is, in the presently preferred embodiment, in the form of a plurality of spray nozzles suitable for dispensing a concentrated solution of potassium permanganate in the form of a fine mist. In FIG. 2, three columns of spray nozzles 24a, 24b and 24c are shown, with each column of spray nozzles including a plurality of vertically spaced nozzles.

The nozzles extend in the vertical direction substantially across the entire height and width of the chamber 14 to insure that the air flow 12a is forced through the spray mist.

Advantageously, the air 12a is deflected by means of inclined guides 26 which deflect the stream of air 12a from its normal direction of flow during the spraying step to maintain the air to be treated under the influence of the potassium permanganate mist 28 for a prolonged period of time for any given rate of flow of the air 12.

The provision of a plurality of spray nozzles as suggested insures that substantially the same concentrations of mist are supplied over the entire cross section of air flow with attendant treatment of all the air which is admitted into the chamber 14.

Since the solution of potassium permanganate is both in the form of a liquid as well as an oxidizing chemical, the passage of the air 12a through the "air scrubber" 22 results in both oxidization as well as washing of the air with respect to the contaminants or odoriferous substances. Many of the larger particles within the air are washed out of the air by the descending liquid spray mist 28 and cause the same to descend into a reservoir 30 which is disposed below the "air scrubber" 22. As mentioned above, most of the odoriferous substances having the smaller molecular weights are also acted upon chemically by the potassium permanganate and the substances are oxidized and eliminated from the air by chemical reaction.

According to another important feature of the present invention, the potassium permanganate solution is recycled through the system within the bath chamber 14. In this manner, substantial amounts of potassium permanganate solution are recycled and utilized more than once to provide the bath for the stream of air.

As described above, a reservoir 30 is disposed at the bottom of the bath chamber 14 and below the array of spray nozzles 24a-24c to receive the potassium permanganate solution when the spray settles and descends under the action of gravity to the bottom of the chamber 14.

When the potassium permanganate solution is recycled in the contemplated manner, the potassium permanganate solution within the reservoir 30 is discharged into a solution purification system generally designated by the reference numeral 32. The purification system includes a receiving chamber 34 which receives the potassium permanganate from the reservoir 30. As suggested above, the solution within the reservoir 30 will contain substances and particles which have been washed out of the stream of air by the spray of the potassium permanganate solution. While the sizes of the particles which are so washed down will vary in size and molecular weight, the bulk of these substances will be of the type which will either float in the solution of the potassium permanganate or sink therein.

A chamber 36 is provided adjacently to the receiving chamber 34, with an opening 40 being provided within the common wall between the two chambers, the opening 40 generally being disposed at a level corresponding to the surface of the liquid within the receiving chamber 34. Those particles which are light, and therefore float on the surface of the liquid in the chamber 34, are transmitted by the spilling liquid into the chamber 36 and removed from the system by means of drain hole 42.

A further chamber 44 is disposed to the other side of the chamber 34, the chambers 34 and 44 sharing a common floor 46 which is inclined as shown. An opening 48 is provided in the lowermost region of the floor 46 through which the heavy particles which have been washed from the air can be drained or removed from the system.

A wall 50 of the chamber 44 extends to the same vertical height as the opening 40 to maintain the fluid at the desired level to permit the spillover through the opening 40 as described above. However, the light particles which flowed at the surface of the fluid are prevented from entering into the chamber 44 by means of a barrier wall or plate 54 which extends below the surface of the liquid. Accordingly, the potassium permanganate solution in the region of the surface thereof in the chamber 44 is purified to the extent that particles of light as well as heavy molecular weights are removed. This solution, which has been purified in the manner described above, is permitted to spill over the wall 50 into a purified fluid collecting chamber 56.

The potassium permanganate solution is, in the presently preferred embodiment, recirculated or recycled so that substantial amounts of potassium permanganate solution are utilized more than once to provide the bath for the stream of air 12a. The system must be replenished with fluid to the extent that this is drained out of the system through the drain openings 42 and 48.

The solution within the chamber 56 is drawn through a return conduit 58 by means of a recirculating pump 60 and directed into a distribution conduit 62 which dispenses the potassium permanganate solution through the columns of spray nozzles 24a, 24b and 24c. While eight spray nozzles are shown spaced from each other in the vertical direction in each of the three columns of such nozzles, it should be clear that the specific number of nozzles in each column and the number of columns is not critical insofar as the present invention is concerned. Any number of columns and any number of nozzles within each column may be utilized as desired as long as the entire stream of air is exposed to the potassium permanganate spray and thereby washed and acted upon chemically to oxidize the odoriferous particles having the smaller molecular weights.

Since potassium permanganate solution is drained from the system, at the openings 42 and 48, and new fluid must be added to the system to replenish the same, there is advantageously provided a potassium permanganate crystal cartridge 64 which dispenses sub-potassium permanganate crystals 66 into the reservoir 30. In this manner, the concentration of the potassium permanganate solution is maintained at substantially a constant high concentration level required for adequate oxidation as described.

When the air 12a has been washed through the "air scrubber" 22, and leaves the bath chamber 14, there is advantageously provided a mist collector 68 which removes the mist or droplets of potassium permanganate solution from the air stream prior to entering the adsorption chamber 18. While the specific construction of the mist collector is not critical, there is shown by way of suggestion only a mist collector which is in the form of a plurality of closely spaced deflecting plates 70. Each of the plates is shown to have a zig-zag cross section. Other mist collectors known in the art may be utilized for this purpose between the two chambers 14 and 18.

The mist collector 68 gathers the droplets forming the spray or mist of the potassium permanganate solution and condenses the same. The condensate flows to the bottom of the mist condenser 68 and is removed from the system by means of a drain opening 72.

The air flow 12b emanating from the mist collector 68 then passes through a bed of activated carbon 74 in which the remaining odoriferous particles having larger molecular weights are substantially removed. As suggested above, the bed of activated carbon may also be useful to remove molecules of smaller molecular weights which have not been or cannot be oxidized by the potassium permanganate bath. The activated carbon is also effective to remove droplets of spray or mist which have not been collected by the collector 68. The air flow 12c to the other side of the activated carbon bed 74 is removed by an air blower 76 through the outlet 20 as indicated by the arrow 12d.

As will be understood from the above description, the air flow 12a includes odoriferous substances having both small and large molecular weights. The air flow 12b, having passed through the "air scrubber" 22 and the mist collector 68, now includes mostly odoriferous substances having large molecular weights, the latter being substantially removed from the air by the bed of activated carbon 74. It has been found that the air 12d which leaves the treatment apparatus 10 is better than 93% pure of foreign matter. This is achieved by utilizing the method and apparatus described above wherein the treatment combines oxidizing, washing and adsorbing the pollutants from the air. However, since the oxidizing and washing is effectively performed in one zone, namely within the bath chamber 14, the present method and apparatus is essentially a two step treatment apparatus which is simple in construction, economical to manufacture, and inexpensive to operate as compared to other comparable treatment devices.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. Apparatus for treating air comprising a first treatment chamber having air inlet means for permitting untreated air containing odoriferous substances of both small and large molecular weight to pass into said first treatment chamber, a second treatment chamber having air exit port means for permitting treated air substantially free of the odoriferous substances to be removed from said second treatment chamber, said first chamber being in air communication with said second chamber to allow air to flow from said inlet means to said exit port means, said second treatment chamber including means for providing a flow of air from said inlet means to said exit port means, said first treatment chamber including a supply of a concentrated solution of potassium permanganate to oxidize the odoriferous substances of the small molecular weight in the untreated air, spray nozzle means disposed in said first chamber for spraying a mist of said solution over the untreated air for both oxidization as well as washing of the untreated air with respect to the odoriferous substances, air guide means disposed in said first chamber and associated with said spray nozzle means for deflecting the flow of air to maintain the untreated air under said spray nozzle means for a prolonged period of time for any given flow rate, said air guide means including a plurality of guide members vertically disposed one above another and inclined upwardly at an angle with respect to a bottom portion of said first chamber, said nozzle means including a plurality of sets of spray nozzles with each set coacting with an associated guide member, said spray nozzles of each set being disposed above its associated guide member at said angle with respect to said bottom portion to allow said untreated air to flow therebetween to provide partially treated air exiting therefrom, reservoir means disposed at said bottom portion of said first chamber below said spray nozzles for receiving said solution containing washed out odoriferous substances after spraying thereof, said reservoir means including a solution purification chamber, said purification chamber including a vertical partition spaced from a bottom wall of said purification chamber to define first and second chamber sections in communication with each other along said bottom wall, said purification chamber including means for allowing said solution to enter said first chamber section to be purified within said purification chamber and second means for allowing a purified solution to exit from said second chamber section, said first chamber section including opening means for allowing floating odoriferous substances to spill therethrough for removal from said purification chamber, said bottom wall being inclined downwardly from said first chamber section to said second chamber section, said bottom wall being provided with drain means to remove heavy odoriferous substances which sink in said concentrated solution from said purification chamber, pump means for recirculating said purified solution from said second chamber section to said spray nozzles, replenish means disposed in said reservoir means for disposing potassium permanganate crystals into said reservoir means to maintain said concentrated solution at a substantially constant level, and said second treatment chamber including adsorbing means to adsorb and remove the odoriferous substances of the large molecular weight in the partially treated air received from said first treatment chamber to provide the treated air.

2. Apparatus as defined in claim 1, wherein said adsorbing means is a bed of activated carbon through which said partially treated air passes.

3. Apparatus as defined in claim 1, wherein said means for providing said flow of air is an air blower disposed at said exit port means.

4. Apparatus as defined in claim 1, wherein means are disposed between said first and second treatment chambers for removing droplets of said concentrated solution from said partially treated air.

* * * * *